United States Patent [19]
Puskas

[11] Patent Number: 6,042,538
[45] Date of Patent: Mar. 28, 2000

[54] DEVICE FOR ENDOSCOPIC VESSEL HARVESTING

[75] Inventor: John D. Puskas, Atlanta, Ga.

[73] Assignee: Emory University, Atlanta, Ga.

[21] Appl. No.: 09/195,782

[22] Filed: Nov. 18, 1998

[51] Int. Cl.[7] ............................... A61B 1/00; A61B 1/32
[52] U.S. Cl. ...................... 600/114; 600/210; 600/235; 606/159; 606/190
[58] Field of Search .................... 600/104, 114, 600/128, 188, 210, 221, 235; 606/159, 1, 190

[56] References Cited

U.S. PATENT DOCUMENTS

| | | | |
|---|---|---|---|
| 2,575,253 | 11/1951 | Bicek | 600/210 |
| 2,944,552 | 7/1960 | Cannon . | |
| 4,793,346 | 12/1988 | Mindich . | |
| 4,873,978 | 10/1989 | Ginsburg . | |
| 5,041,091 | 8/1991 | Herring . | |
| 5,304,184 | 4/1994 | Hathaway et al. . | |
| 5,373,840 | 12/1994 | Knighton . | |
| 5,400,768 | 3/1995 | McNamara et al. | 600/104 |
| 5,448,990 | 9/1995 | De Faria-Correa . | |
| 5,476,469 | 12/1995 | Hathaway et al. . | |
| 5,591,183 | 1/1997 | Chin . | |
| 5,593,418 | 1/1997 | Mollenauer . | |
| 5,601,581 | 2/1997 | Fogarty et al. . | |
| 5,667,480 | 9/1997 | Knight et al. . | |
| 5,695,514 | 12/1997 | Chin . | |
| 5,730,748 | 3/1998 | Fogarty et al. . | |
| 5,759,150 | 6/1998 | Konou et al. | 600/114 |
| 5,797,947 | 8/1998 | Mollenauer . | |
| 5,846,249 | 12/1998 | Thompson | 600/221 |

FOREIGN PATENT DOCUMENTS

1371689 A1  2/1988  U.S.S.R. .

OTHER PUBLICATIONS

Lumsden, et al., "Vein Harvest," *Endoscopic Plastic Surgery*, pp. 535–543.

Meldrum–Hanna, et al., "Long Saphenous Vein Harvesting," *Aust. N.Z. J. Surg.*, vol. 56, pp. 923–924 (1986).

Dimitri, et al., "A Quick and Atraumatic Method of Autologous Vein Harvesting Using the Subcutaneous Extraluminal Dissector," *J. Cardiovasc. Surg.* vol. 28, pp. 103–111 (1987).

Hauer, et al., "Endoscopic Subfascial Discission of Perforating Veins," *Surg. Endosc.* vol. 2, pp. 5–12 (1988).

*Primary Examiner*—John P. Leubecker
*Attorney, Agent, or Firm*—Jones & Askew, LLP

[57] ABSTRACT

A endoscopic device provides improvements in the endoscopic working space by the use of a semi-tubular hood with an arched top wall and self-supporting walls that allow simultaneous manipulations of dissection, cutting, ligation, and retraction, and the like, without requiring constant application of external force; while enhancing visualization and reducing the need for cleaning the endoscopic lens.

20 Claims, 4 Drawing Sheets

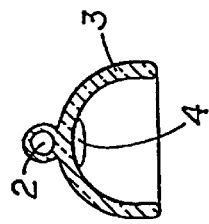
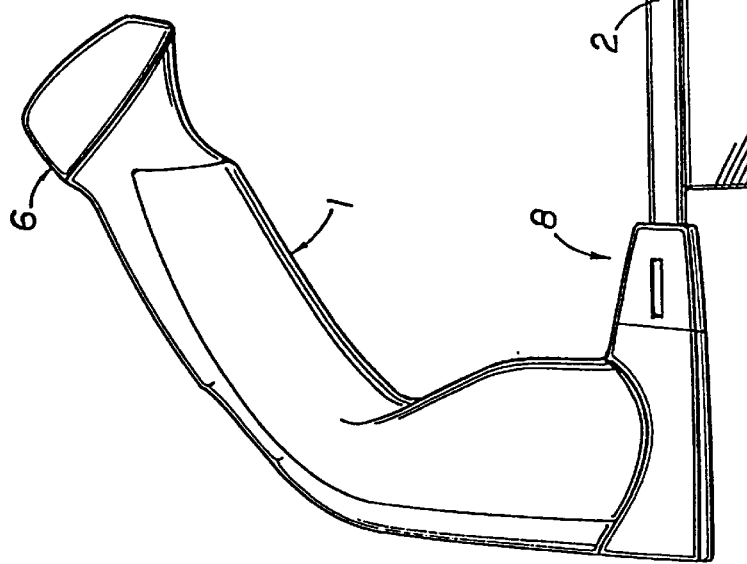
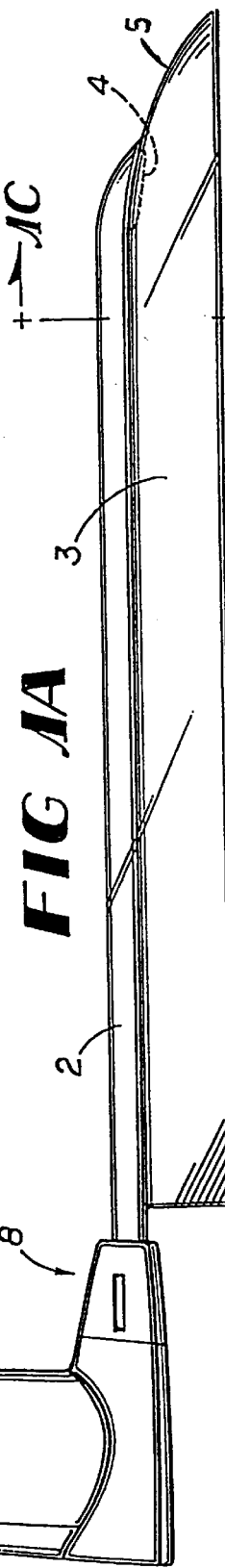
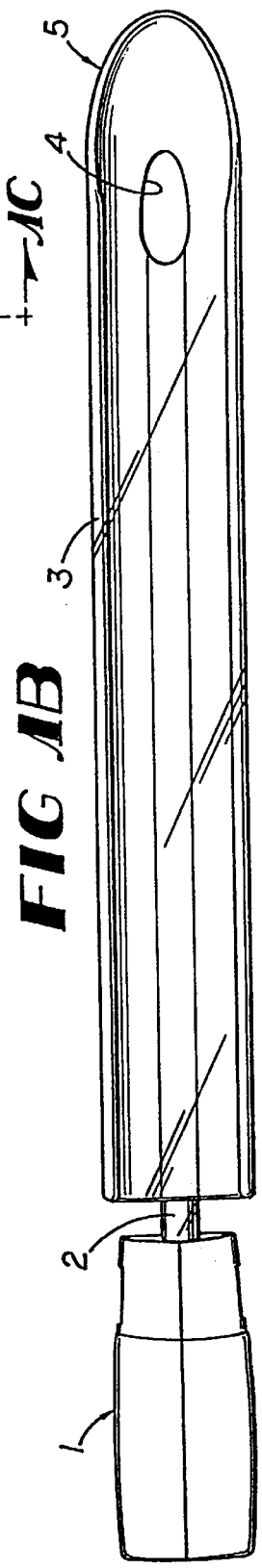

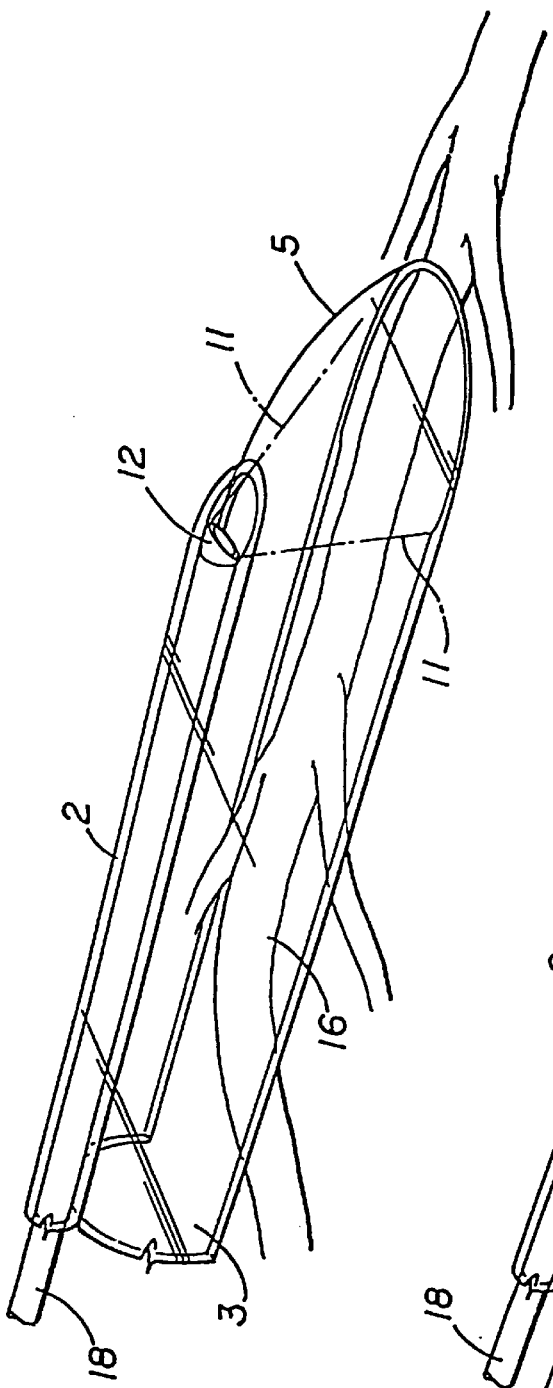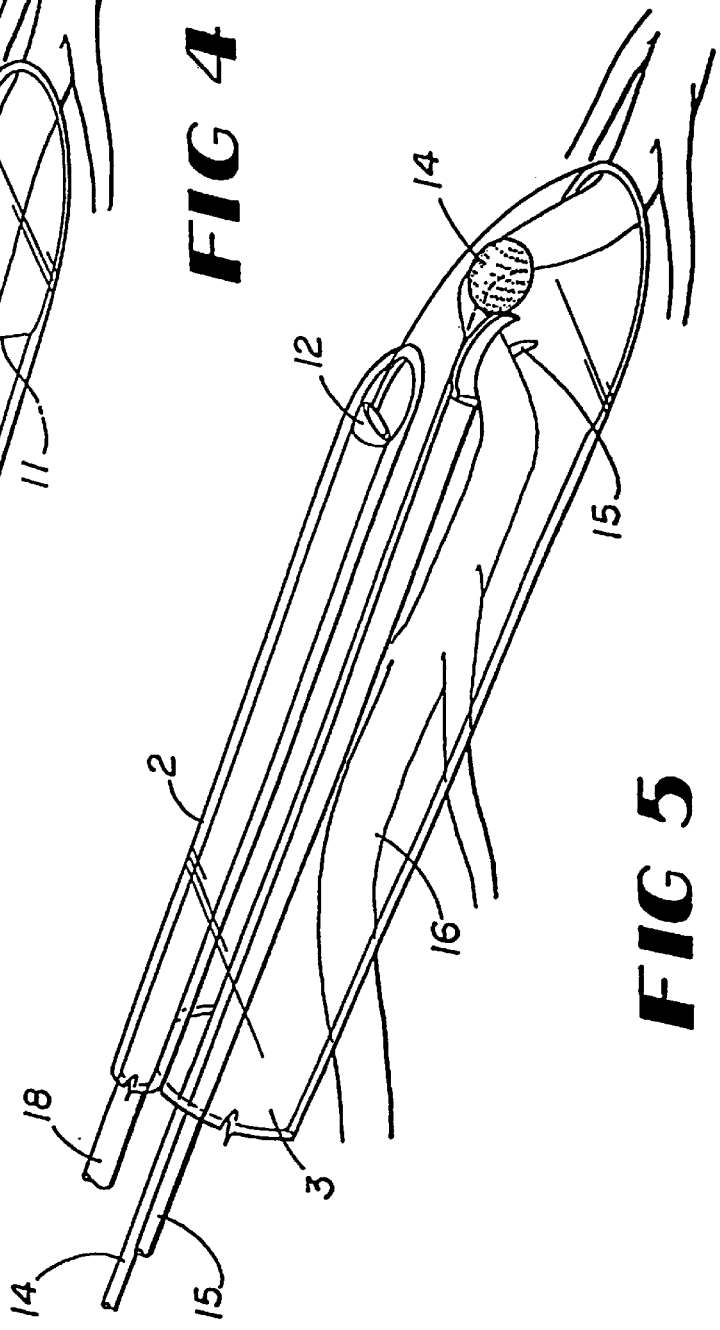

6,042,538

DEVICE FOR ENDOSCOPIC VESSEL HARVESTING

BACKGROUND OF THE INVENTION

Vessel harvesting has traditionally required skin incisions as long as the length of the vessel removed. This technique produces long scars and may result in healing-difficulties. The present invention addresses the need for less invasive removal of vessels. It is adaptable to a wide variety of surgical procedures, including harvesting saphenous vein for peripheral vascular surgery or for coronary artery bypass grafting.

Generally, minimally invasive vessel harvesting with an endoscope is known in the surgical field. In one procedure, a vessel is removed with an endoscope having a lumen therethrough. In this procedure, the saphenous vein is held with a grasper which is introduced through the lumen of the endoscope. After connective tissue has been dissected from around the vein, the vein is then ligated and transected and removed from the lower limb of the patient through the lumen of the endoscope. See, SU 1371689.

Although this method provides for a minimally invasive technique, there are several associated drawbacks. First, in practicing this method there is limited visibility of the saphenous vein and its side branches because viewing is limited to the immediate area directly in front of the endoscope. Secondly, the illumination within the subcutaneous space created by this type of endoscope is also limited to the light emitted directly at the distal portion of the endoscope. Another drawback is that the side branches of the saphenous vein limit the maneuverability of the endoscope since the outer edge of the endoscope body is prevented from advancing along the trunk of the saphenous vein until the encountered side branches are ligated and transected thereby. Perhaps most important, methods which utilize this type of endoscope, i.e. an endoscope having a lumen, provide a working space which is very restricted because the side walls of the scope body confine the working instrumentation to a very limited area. An additional problem is that the lens of the endoscope becomes soiled after touching tissue, so it must be withdrawn and cleaned periodically during vessel dissection and retraction.

Furthermore, the vessel harvesting method described above is typically a three-handed approach which actually requires more than one individual. In this method, one hand is required to hold and maintain the endoscope in position, while a second hand is required to hold the free end of the transected vessel with a grasper and a third hand is required to dissect connective tissue away from the vessel.

Another method for harvesting the saphenous vein is disclosed in "Vein Harvest", Alan B. Lumsden and Felmont F. Eaves, III, in Endoscopic Plastic Surgery (Quality Medical Publishing, Inc., 1995), pp. 535–543. This method provides for performing a preliminary dissection of the saphenous vein while using an open technique prior to inserting an endoscopic retractor such as those commonly used in plastic surgery. In this procedure, once the subcutaneous tissue is retracted with the endo-retractor, a pair of scissors is used to dissect the superior surface of the saphenous vein in order to expose the vein.

A method using both an optical dissector and an optical retractor has been described for endoscopic removal and harvesting of blood vessels. See U.S. Pat. No. 5,667,480. The devices described therein need frequent cleaning of the small endoscopic lens during harvesting, due to the shallow working space beneath the platform and the position of the endoscope within the working head and platform. Also, when multiple instruments, such as a dissector and a retractor, are needed to perform harvesting, they must be inserted beneath the endoscope and outside of the platform passageway. This requires manually lifting the device, which can cause injury to the target vessel and fatigue to the operator. The harvesting devices lack a long semi-tubular hood having side walls that lends numerous advantages to the present invention.

Applicant has devised an apparatus that avoids many of the disadvantages of known methods. Applicant attaches a self-supporting, full-length semi-tubular hood to the shaft containing the endoscope. The hood provides easy access to any subcutaneous site while elevating the downward looking endoscope above and away from tissues so that it is less commonly soiled, thereby avoiding periodic cleaning of the endoscopic lens. Various instruments, such as endo-scissors, endo-staplers, retractors or dissectors, may be easily inserted within the semi-tubular hood during harvesting without withdrawing the entire device.

SUMMARY OF THE INVENTION

Applicant has devised an apparatus for removing vessels and arteries from the patient with minimally invasive procedures. The apparatus has a self-retaining, full-length semi-tubular hood attached to a shaft that is inserted into a small incision through the skin to provide and maintain a generous work space and permits the easy insertion and use of a variety of surgical instruments simultaneously, e.g., a dissector and retractor.

Accordingly, it is an object of the present invention to provide an improved endoscopic device, especially useful for dissecting veins or arteries.

It is a further object of the present invention to provide an endoscopic device that permits the passage therethrough and maneuverability therein of multiple instruments.

It is a further object of the present invention to provide an endoscopic device that permits more downward viewing of the target tissues, with less frequent need for retraction and cleaning of the endoscope.

It is a further object of the present invention to provide an endoscopic device for dissecting veins or arteries that minimizes damage to the target tissues.

BRIEF DESCRIPTION OF THE DRAWINGS

FIG. 1A schematically illustrates a side view of the device of the present invention, with handle and semi-tubular hood.

FIG. 1B schematically illustrates a bottom view of the device of the present invention.

FIG. 1C schematically illustrates a cross-section of the device of the present invention.

FIG. 4 schematically illustrates an enlarged perspective view of the distal end of the tool placed over an exposed vessel.

FIG. 5 schematically illustrates the perspective view of FIG. 4 with endo-scissors and dissector placed together to work within view of the endoscope.

DETAILED DESCRIPTION OF THE INVENTION

Figures 2, 3:
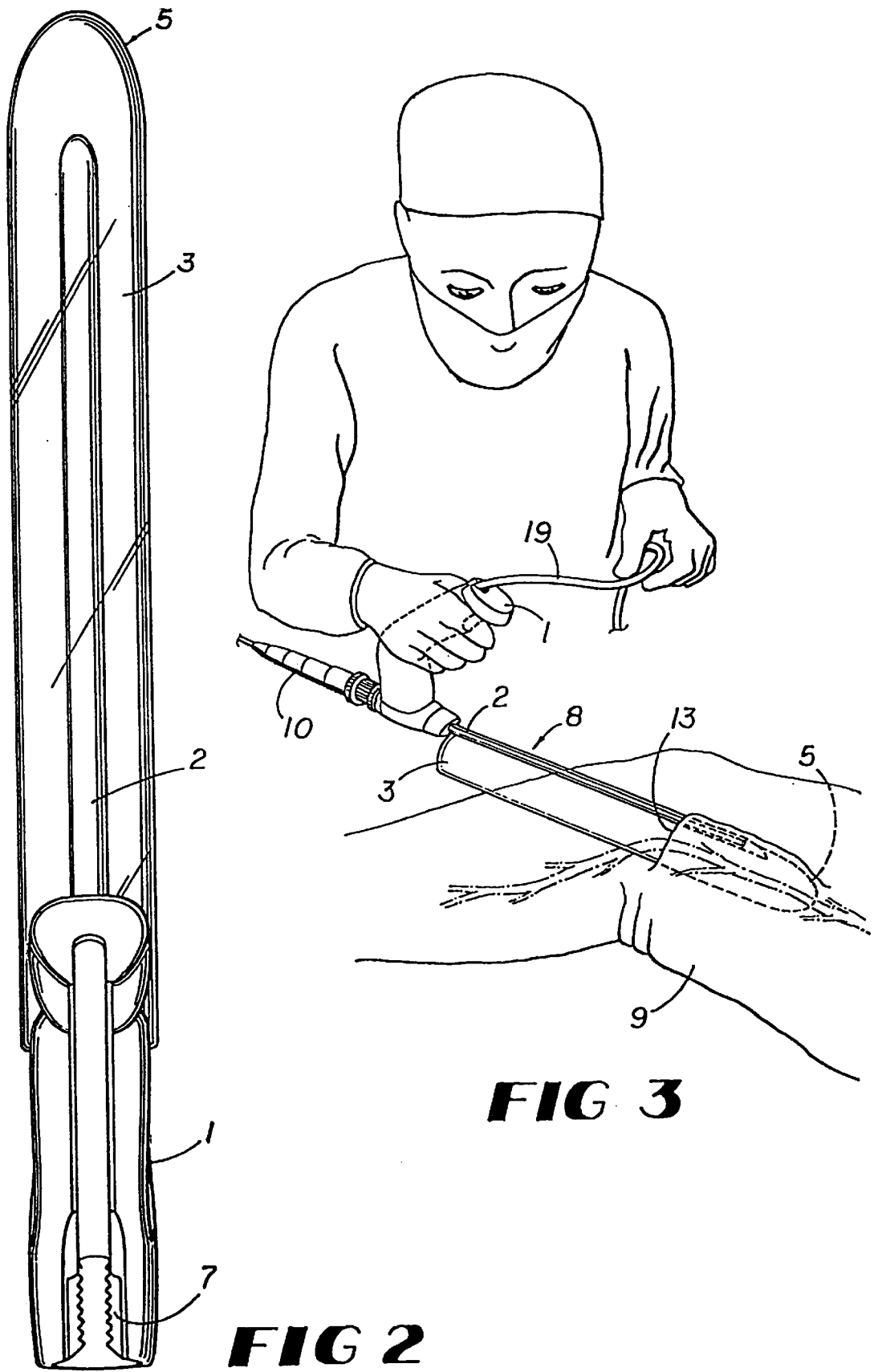
FIG. 2 schematically illustrates a top view of the device of the present invention.
FIG. 3 schematically illustrates a surgeon in the process of inserting the device of the invention through an incision of the patient's leg.

The device of the present invention allows a generous working space for endoscopic surgery, for example dissection and retraction of blood vessels, e.g., the saphenous vein for vessel harvesting. One embodiment of the device of the present invention is set forth by way of example in FIGS. 1A, 1B and 1C. FIG. 1A is a side view of device 8 showing a shaft 2 attached to a semi-tubular hood 3 and opening 4 for insertion (beginning with tip 5) into the subcutaneous space after incision of the skin over the vessel to be removed. FIG. 1A lacks an endoscope. However, any endoscope, as shown as 18 in FIG. 4, may be inserted into the shaft 2 (or even through the semi-tubular hood 3) for viewing further surgical manipulations taking place beneath the opening 4, including dissection, ligation, stapling and retraction. An optional handle 1 provides convenient manual positioning by the surgeon, the endoscope fiber optic wire (shown as 19 in FIG. 3) protruding out of the top 6 of the handle. A bottom view of the device 8 of the present invention is schematically illustrated, in one embodiment of the present invention, as FIG. 1B. The bottom is supported by the side walls of the semi-tubular hood and is otherwise open.

The semi-tubular hood preferably extends over the full length of the endoscope shaft, or at least the length thereof that is to be inserted into the patient. The side walls of the semi-tubular hood 3 support the top and retain the generous working space without requiring application of external force to insert auxiliary instruments therein. By a generous working space within the semi-tubular hood is meant that at least one, or preferably at least two, separate instruments can be inserted therein simultaneously with the endoscope in place. For example, a retractor and an excisor will preferably fit within the semi-tubular hood area, and the target tissues can be viewed with the endoscope while work is being performed. A cross-sectional view of the device 8 of the present invention is schematically illustrated in FIG. 1C, showing such a generous working space, without the auxiliary instruments therein.

The semi-tubular hood 3 support thus creates a tunnel space for the insertion and removal of instruments to assist in the dissection of veins and arteries. Preferably, the top wall of the semi-tubular hood has an arc of greater than 120°, more preferably greater than 150°, and most preferably about 180° across the top. The side walls may extend in a downward direction from the arc to a length varying depending upon the length and depth of the vessels to be removed and the relative size of the patient. The side walls terminate in smooth, rounded bottom edges so as to be atraumatic to the adjacent tissues. The dimensions of the side walls varies according to the length and depth of the vessel to be removed, the size of the patient, and the relative obesity of the patient. The height of the side walls, excluding the added height from the top wall (at least about 0.5 cm), varies between about 0.5 cm and about 7.5 cm, preferably between about 1.5 cm and about 3.0 cm, most preferably about 2.5 cm. For obese patients, the preferred height of the side walls is greater, i.e., between about 2.5 cm and about 5.0 cm.

A top view of one embodiment of the device of the present invention is set forth in FIG. 2, showing semi-tubular hood 3, handle 1, shaft 2, and concave head as device tip 5. A hatched area 7 secures the cord for the endoscope, and is typically made of rubber.

A surgeon is shown in FIG. 3 inserting the device 8 of the present invention through an incision 13 in the skin of the patient's leg 9. The semitubular hood 3, power source 10, and endoscopic fiber optic wire 19 are shown. It is readily apparent from this figure that the size of the device 8 will depend on the size and location of the blood vessel to be removed, as well as the relative obesity of the patient. The entire arrangement permits a two-handed procedure, unlike known protocols in the art, because the semi-tubular hood maintains the working space along the length of the endoscope.

FIG. 4 schematically illustrates, in one embodiment of the present invention, an enlarged perspective view of the distal end of the device placed over an exposed vessel. The downward looking scope 12 is shown immediately over the working area defined by phantom lines 11 in the field of endoscopic vision. This embodiment also shows that the shaft 2 is placed on top of the semi-tubular hood 3, but other embodiments include a shaft placed inside of the semi-tubular hood, e.g., attached to the inside and the top of the semi-tubular hood. The generous working space beneath the semi-tubular hood 3 and over the exposed blood vessel provides many practical advantages in surgical procedure.

FIG. 5 schematically illustrates, in one embodiment of the present invention, an enlarged perspective view of the distal end of the device, placed over an exposed vessel, as in FIG. 4, but with dissector 14 and endo-scissors 15 shown inserted and placed in the work space of the device. The dissector here is a disposable rod with a spool of fibrous material at the end for wrapping and withdrawal of the dissected vessel. Endo-scissors 15 here are a disposable rod with a small pair of sheers at the terminal end embracing a blood vessel to be cut. Also shown are the shaft 2, semi-tubular hood 3, the endoscope 18 and its downward looking scope 12 and blood vessel 16 to be harvested. It is readily apparent that a variety of other instruments can be inserted into the working space under the semi-tubular hood 3. For example, retractors, endo-staplers, suction devices, electric or ultrasonic cantory devices, blowers, as well as various other types of dissectors can be inserted without withdrawing the entire device from the underneath the skin of the patient.

Figure 6:
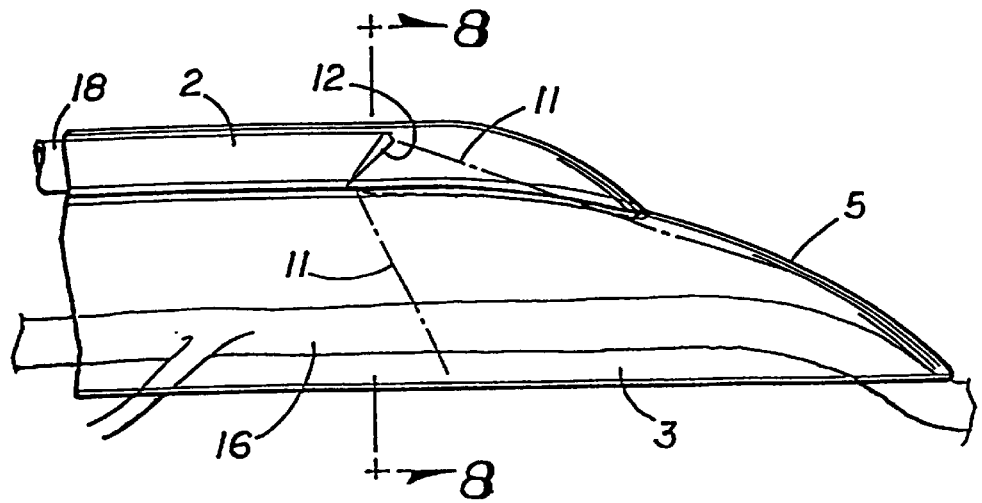
FIG. 6 schematically illustrates a side elevation of the tool tip showing phantom lines for the field of endoscopic vision of the enlarged work space.

FIG. 6 schematically illustrates, in one embodiment of the present invention, a side elevation of the device tip, showing phantom lines 11 for the field of endoscopic vision of an enlarged workspace. The downward looking scope 12 and exposed blood vessel 16 are also shown.

Figure 7:
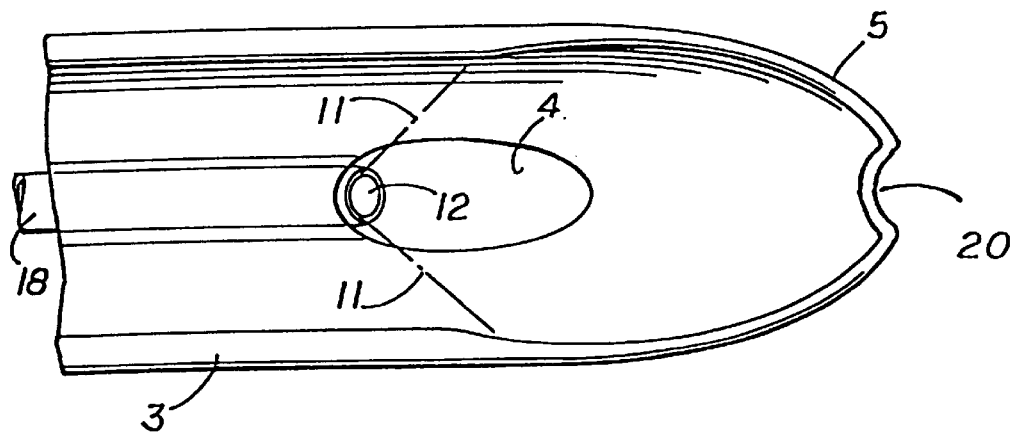
FIG. 7 schematically illustrates a bottom plan view of the tool tip of FIG. 6.

FIG. 7 schematically illustrates, in one embodiment of the present invention, a bottom plan view of the tool tip of FIG. 6. The downward looking scope 12 with phantom lines 11 for the field of endoscopic vision are shown. In one embodiment, the leading edge of the tip or spoon has an indentation 20 to accommodate the curvature of the vessel being harvested.

Figure 8:
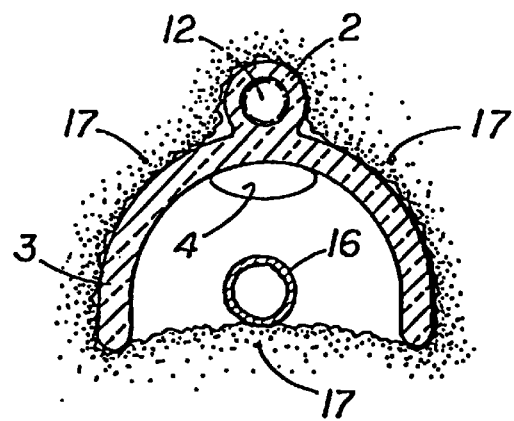
FIG. 8 schematically illustrates a transverse cross-section taken along the lines 8—8 in FIG. 6, with (stippled) fat encompassing the tool.

FIG. 8 schematically illustrates, in one embodiment of the present invention, a transverse cross-section taken at 8—8 of FIG. 6, when the device is inserted under the skin of a patient's leg. Also illustrated are the semi-tubular hood 3, downward looking scope 12, exposed blood vessel 16, and fat 17 shown as stippling.

The semi-tubular hood 3 is preferably made of transparent plastic, or stainless steel. Preferably, it is made of transparent plastic, making it less costly. A steel strut may be inserted into the shaft 2 or the back of the semi-tubular hood 3 to minimize bending or other deformation of the device during use.

The dimensions of the semi-tubular hood 3 vary according to the length and depth of the vessel to be removed, the size of the patient, and the relative obesity of the patient. The height of the semi-tubular hood 3, excluding the added height from the attached shaft (about 0.5 cm), varies between about 1.5 cm and about 5.0 cm, preferably between about 2.0 cm and about 3.0 cm, most preferably about 2.5 cm. For obese patients, the preferred height of the semi-tubular hood 3 is greater, i.e., between about 3.0 cm and about 5.0 cm.

The semi-tubular hood 3 is attached to the length of the shaft 2, but need not have the same length as the shaft 2. The length of the semi-tubular hood 3 (excluding the spoon at the tip 5, about 5 cm) may vary between about 15 cm and about 45 cm, preferably between about 20 cm and about 31 cm, most preferably about 25 cm. The shaft 2 need not be attached on top and outside of the semi-tubular hood 3, but instead may be attached to the top of the inside of the semi-tubular hood 3. The preferred arrangement is a shaft attachment to the top and outside of the semi-tubular hood 3, to increase the size of the access to the work space beneath the downward looking endoscope 12.

The width of the semi-tubular hood 3 is the breadth across the bottom of the semi-tubular hood 3 on the side opposite to the side of the semi-tubular hood 3 with the endoscope 18 and attached shaft 2. The width may vary according to the length of vessel to be removed, and the size and relative obesity of the patient. Width may vary between about 2.0 cm and about 5.0 cm, preferably between about 2.0 cm to about 3.0 cm. For obese patients, a greater width is typically desirable, e.g., between about 2.0 cm and about 4.0 cm. Furthermore, the width may vary in a single device, such that the semi-tubular hood 3 tapers in width.

The shaft 2 houses the endoscope, and should be big enough to only snugly fit the endoscope 18 without rattling. The shaft 2 is not completely in the working space of the semi-tubular hood, but rather lies in the wall or above the wall of the semi-tubular hood. A device 8 with the appropriate shaft inner diameter is selected for the appropriate endoscope. The inner diameter of the shaft 2 will vary according to the size of the endoscope 18, and may range between about 2 mm and about 5 mm. Typical endoscopes currently in use are fiber optic quartz rods of about 30 cm in length, with about 5 mm in diameter. Other endoscopes are cables with substantially smaller diameter, e.g., about 2 mm. The device of the present invention is adaptable to various types of endoscopes, and fashioning the correct shaft dimensions of the device is within the skill of the art. Endoscopes with a downward looking scope 12 with an angle of between about 0° and about 90° are preferred, more preferred are endoscopes with a downward looking scope 12 with an angle of between about 30° and about 60°, and most preferred are endoscopes with a downward looking scope 12 with an angle of between about 45° The invention is able to utilize an endoscope with a greater downward looking angle than prior similar instruments, due to the increase in depth of working space within the semi-tubular hood. This configuration permits the endoscope to remain more clear of debris, minimizing the number of withdrawals for cleaning during a procedure.

In the techniques of the present invention, an incision in the skin of about 3–4 cm in length is made in the patient's leg near the identified vessel. Device 8 is inserted along and above the vessel 13 to be harvested. A dissector, e.g., 14, is then inserted through the incision and tissue is then dissected away from the superior surface of the vessel as the dissector is manipulated along the surface of the vessel under direct visualization.

After the initial dissection of the superior surface of the vessel by the dissector, the dissector may be withdrawn and replaced with a retractor which is also inserted through the incision and advanced under the semi-tubular hood. Alternatively, the dissector may remain under the semi-tubular hood. At this point, endo-scissors may be inserted, as shown in FIG. 5, or any other appropriate instrument, including a retractor, and endo-stapler, a suction or cautery apparatus, or blower device. In the process of removing or harvesting a blood vessel, side branches of the vessel are dissected, ligated and transected within the working space provided by the device of the present invention. After transection of the proximal and distal ends of the vessel, the vessel may be removed through the incision and can be used in a bypass or grafting procedure.

In one preferred embodiment of the present invention, the device 8 can function as both a dissector and a retractor, thus eliminating the need for two devices, i.e., an endoscopic dissector and an endoscopic retractor. The device 8 of the present invention accommodates an endoscope 18 with a downward looking scope 12 with an angle of between about 0° and about 90°, preferably between about 30° and about 60°, most preferably 45°. Such an increased downward looking angle permits the endoscope to remain relatively more clear of debris during the procedure, which thus permits less frequent withdrawal and cleaning of the endoscope.

It is apparent that the endoscopic device of the present invention can be used in a variety of surgical procedures in addition to blood vessel harvesting, such as peripheral vascular surgery, excision of subcutaneous masses including lymphomas, or in situ saphenous vein by-pass grafting for peripheral vascular disease, for example.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

I claim:

1. An endoscopic device, comprising:
   a. a shaft having a lumen therethrough for receiving an endoscope;
   b. a semi-tubular hood having an arched top wall connected to the shaft and self-supporting side walls extending from the arched top wall, wherein the semi-tubular hood permits the separation of layers of tissue during dissection and maintains a generous working space capable of receiving at least one additional surgical instrument therein, and, wherein the shaft is exterior to the top and working space of the semi-tubular hood, thereby not impinging on the working space within the semi-tubular hood; and,
   c. a concave head connected to a distal end of the semi-tubular hood, the head having a spoon-shape and defining a cavity thereunder.

2. The device of claim 1, further comprising a handle connected to the shaft or to the semi-tubular hood at the proximal end of the shaft or semi-tubular hood.

3. The device of claim 1, further comprising an endoscope in the shaft, wherein the endoscope has a viewing angle of between about 30° and about 60° relative to the shaft.

4. The device of claim 1, further comprising an endoscope in the shaft, wherein the endoscope has a viewing angle of about 45° relative to the shaft.

5. The device of claim 1, wherein the spoon-shaped head has an indentation at its leading edge to accommodate a vessel to be harvested.

6. The device of claim 1, wherein the semi-tubular hood extends the full length of the shaft.

7. The device of claim 1, wherein the top wall of the semi-tubular hood has an arc of greater than 120°.

8. The device of claim 1, wherein the top wall of the semi-tubular hood has an arc of about 180°.

9. The device of claim 1, wherein the side walls extend from the top arched wall for a length of between about 0.5 cm to about 7.5 cm.

10. An endoscopic device, comprising:
   a. a shaft having a lumen therethrough for receiving an endoscope;
   b. a semi-tubular hood having an arched top wall connected to the shaft and self-supporting side walls extending from the arched top wall, wherein the semi-tubular hood permits the separation of layers of tissue during dissection and maintains a generous working space capable of receiving at least one additional surgical instrument therein; and,
   c. a concave head connected to a distal end of the semi-tubular hood, the head having a spoon-shape and defining a cavity thereunder, and wherein the spoon-shaped head has an indentation at its leading edge to accommodate a vessel to be harvested.

11. The device of claim 10, further comprising a handle connected to the shaft or to the semi-tubular hood at the proximal end of the shaft or semi-tubular hood.

12. The device of claim 10, further comprising an endoscope in the shaft, wherein the endoscope has a viewing angle of between about 30° and about 60° relative to the shaft.

13. The device of claim 10, further comprising an endoscope in the shaft, wherein the endoscope has a viewing angle of about 45° relative to the shaft.

14. The device of claim 10, wherein the semi-tubular hood extends the full length of the shaft.

15. The device of claim 10, wherein the shaft is in or exterior to the top wall of the semi-tubular hood, thereby not impinging on the working space within the semi-tubular hood.

16. The device of claim 10, wherein the top wall of the semi-tubular hood has an arc of greater than 120°.

17. The device of claim 10, wherein the top wall of the semi-tubular hood has an arc of about 180°.

18. The device of claim 10, wherein the side walls extend from the top arched wall for a length of between about 0.5 cm to about 7.5 cm.

19. The device of claim 10, further comprising an endoscope in the shaft, wherein the endoscope has a viewing angle of between about 0° and about 90° relative to the shaft.

20. The device of claim 1, further comprising an endoscope in the shaft, wherein the endoscope has a viewing angle of between about 0° and about 90° relative to the shaft.

* * * * *